US006790203B2

(12) United States Patent
Eén

(10) Patent No.: US 6,790,203 B2
(45) Date of Patent: Sep. 14, 2004

(54) ABSORBENT PRODUCT COMPRISING LEAKAGE BARRIERS

(75) Inventor: Hans Eén, Mölnlycke (SE)

(73) Assignee: SCA Hygiene Products AB, Gothenburg (SE)

( * ) Notice: Subject to any disclaimer, the term of this patent is extended or adjusted under 35 U.S.C. 154(b) by 0 days.

(21) Appl. No.: 10/022,738

(22) Filed: Dec. 20, 2001

(65) Prior Publication Data

US 2003/0093053 A1 May 15, 2003

Related U.S. Application Data

(60) Provisional application No. 60/256,488, filed on Dec. 20, 2000.

(51) Int. Cl.[7] .......................... A61F 13/15; A61F 13/20
(52) U.S. Cl. .................. 604/385.28; 604/364; 604/365
(58) Field of Search .................. 664/385.24–385.3, 664/364–367, 392–396

(56) References Cited

U.S. PATENT DOCUMENTS

| | | | |
|---|---|---|---|
| 4,695,278 A | | 9/1987 | Lawson |
| 4,822,435 A | | 4/1989 | Igaue et al. |
| 4,904,251 A | | 2/1990 | Igaue et al. |
| 5,021,051 A | * | 6/1991 | Hiuke .................. 604/385.27 |
| 5,064,489 A | | 11/1991 | Ujimoto et al. |
| 5,454,803 A | * | 10/1995 | Sageser et al. ........ 604/385.28 |
| 5,527,303 A | * | 6/1996 | Milby et al. ........... 604/385.16 |
| 6,120,488 A | * | 9/2000 | VanRijswijck et al. 604/385.28 |
| 6,506,187 B1 | * | 1/2003 | Andersson et al. .... 604/385.28 |
| 6,565,549 B1 | * | 5/2003 | Allen et al. |

FOREIGN PATENT DOCUMENTS

| | | |
|---|---|---|
| EP | 517548 | 12/1992 |
| GB | 2188532 | 10/1987 |
| SE | 264238 | 9/1991 |
| WO | 92/07533 | 5/1992 |

OTHER PUBLICATIONS

"Fatty Acids", The Materials Handbook, pp 318–320.*
CRC Handbook of Chemistry and Physics, 75th edition, 1994–1995, p. 7–28, 7–29.
F.J. Akin et al., Skin Research & Technology, 1997; 3:173–176.

* cited by examiner

Primary Examiner—K. M. Reichle
(74) Attorney, Agent, or Firm—Burns, Doane, Swecker & Mathis, L.L.P.

(57) ABSTRACT

An absorbent product has an absorption body with a generally oblong shape with two longitudinal sides, two transverse sides, a longitudinal center line, and also includes a first, liquid-permeable surface layer and a second, essentially liquid-impermeable surface layer, an essentially liquid-impermeable backing layer, an absorption body positioned between the liquid-permeable surface layer and the backing layer, two leakage barriers made of flexible material in the longitudinal direction on each side of the longitudinal center line. Each leakage barrier has a first edge permanently fastened along the first, liquid-permeable surface layer and a second edge which extends in the direction of the longitudinal center line of the absorbent product. The first surface and/or the second surface of each leakage barrier is fastened to or near to the first, liquid-permeable surface layer and/or the second, liquid-impermeable surface layer.

26 Claims, 4 Drawing Sheets

ABSORBENT PRODUCT COMPRISING LEAKAGE BARRIERS

CROSS-REFERENCE TO RELATED APPLICATION

This application claims the benefit under 35 U.S.C. § 119(e) of U.S. Application Serial No. 60/256,488 filed on Dec. 20, 2000; the entire content of which is hereby incorporated by reference.

FIELD OF THE INVENTION

The invention relates to an absorbent product, such as a diaper, a pant diaper, an incontinence pad, a sanitary towel or the like. The absorbent product has an absorption body with a generally oblong shape including two longitudinal sides, two transverse sides, a longitudinal center line, a transverse center line, and also including a first, liquid-permeable surface layer and a second, liquid-impermeable surface layer, a liquid-impermeable backing layer, an absorption body positioned between said liquid-permeable surface layer and said backing layer, two leakage barriers made of flexible material in the longitudinal direction on each side of the longitudinal center line and the first, liquid-permeable surface layer, each of the leakage barriers having a first edge permanently fastened along the first, liquid-permeable surface layer and a second edge which extends mainly in the direction of the longitudinal center line of the absorbent product, each of the leakage barriers also having a first surface and a second surface.

BACKGROUND OF THE INVENTION

In order to prevent the risk of leakage at the side edges of an absorbent product, some absorbent products have what are known as standing or raised leakage barriers, also referred to as inner liquid barriers, standing barriers or cuffs, in most cases fastened in association with a liquid-permeable surface layer on the product. The function of the leakage barrier is to prevent liquid leaking out at the edges of the absorbent product and, if appropriate, to prevent leakage of solids such as excrement. These leakage barriers are located inside the leg elastic, which shapes the product and constitutes an outer liquid barrier, also referred to as the outer leakage barrier, and are usually made of an essentially liquid-impermeable material, for example fiber fabric, which is also known as non-woven. Sometimes, the barriers can also be made of liquid-permeable material. The leakage barriers are formed by a web, one longitudinal edge of which is fastened to the absorbent product and the other, free edge of which is intended to bear against the wearer. The free edge is elastically gathered by means of an elastic thread which is incorporated into the edge of the web. Examples of absorbent articles with leakage barriers (or what are known as liquid barriers) are described in, for example, WO-A1-9207533, U.S. Pat. No. 4,695,278, U.S. Pat. No. 5,064,489, SE-T3-0264238 and GB-A-2188532. When the absorbent product has leakage barriers arranged inside flexible side flaps on both sides of the absorption body of the product, it is usual for the surface material between the two inner leakage barriers, that is to say in the liquid-receiving area, to be liquid-permeable, while the surface material outside the leakage barriers is essentially liquid-impermeable.

On diapers with what are known as inner leakage barriers, for example, the barrier will, during use, be positioned so that it bears against the leg and buttocks of the wearer and is to prevent leakage there. Each time urine is discharged into the diaper, a certain quantity comes into contact with the wearer. It takes a little time before the urine penetrates the surface layer and is absorbed in the absorbent layer, so a certain volume of urine will flow in the absorbent product on top of the surface layer. This is the volume which the barrier is to prevent leaking out at the edges of the absorbent product.

New problems arise precisely because of the purpose and material characteristics of the leakage barriers. The leakage barriers, which are essentially liquid-impermeable, can, when the product is put on the wearer, lie over the liquid-permeable surface layer instead of fitting tightly around the thighs and buttocks of the wearer. This may be as a result of the product having been tightened too firmly, incorrectly, carelessly or the like. When a leakage barrier lies incorrectly, there may be unfavourable consequences in the form of poor fit and unoptimized dimensional stability. The greatest problem, however, is in the increased risk of leakage. There are two main reasons for increased leakage, the first being that the leakage barriers are no longer positioned where they are intended to be, which can give rise to openings between the thighs of the wearer and the product, where liquid can escape. The second is that the leakage barriers can lie on the liquid-permeable surface layer and thus prevent the liquid from being admitted into and absorbed in the absorption body. Instead, the liquid runs on or via the liquid-impermeable surface of the leakage barriers, and thus gives rise to leakage and discomfort.

For bedridden wearers, the problem is marked when the person fitting the absorbent product may perhaps be unable to arrange everything properly. The wearer may be, for example, a heavy person, while the person applying the product might not have sufficient strength in order to perform all the necessary lifting and turning. This means that it is important to ensure everything is correct the first time the absorbent product is put on, so that no further action has to be taken.

The problem of leakage barriers lying incorrectly is especially marked with an absorbent product with a narrow crotch portion, that is to say the distance between the longitudinal sides of the absorption body is relatively small. The leakage barriers may then cover a greater percentage of the area of the liquid-permeable surface layer and thus indirectly of that surface of the absorption body facing the wearer than if the distance between the longitudinal sides of the absorption body is relatively great. In the same way, a high leakage barrier, that is to say a barrier where the distance between the longitudinal edges of the leakage barrier is great, can cover a greater percentage of the area of the liquid-permeable surface layer and thus indirectly of the absorption body than if the distance between the longitudinal edges of the leakage barrier is small.

An object of the invention is to solve these problems in a refined manner which is comfortable for the wearer.

SUMMARY

According to one embodiment of the claimed invention, an absorbent product of the type mentioned in the introduction has been produced, which product essentially eliminates the problems associated with previously known such products. The first surface and/or the second surface of each leakage barrier is fastened to or near to the first, liquid-permeable surface layer and/or the second, liquid-impermeable surface layer.

According to one embodiment, the first surface and/or second surface of each said leakage barrier is temporarily fastened by a binder which loses its adhesive and/or cohesive capacity during use of the absorbent product, the first surface and/or second surface of each leakage barrier then coming away from its fastening surface and becoming a raised leakage barrier.

A binder can be an agent which has an adhesive and/or cohesive capacity, for example glue or wax, but it is also possible to use a binder such as, for example, ultrasonic welding and thermal welding.

Here and henceforth, the term fastening surface means one or more surfaces to which the binder (which is intended to lose its adhesive and/or cohesive capacity during use) is applied on the leakage barriers. The surface or surfaces where the binder is applied, that is to say the fastening surface, can in principle have any shape and be positioned in one or more different places on the leakage barriers. Here and henceforth, the term fastening surface does not therefore contain any limitation in terms of the number or shape of fastening surfaces.

It is of course impossible to avoid an interaction among various parameters, for example temperature, atmospheric humidity, choice of material, tensile forces or shear forces etc., which together contribute to a binder losing its adhesive and/or cohesive capacity, but it is in most cases possible to distinguish the major influencing factor. Here, a major influencing factor means a factor which, without the other factors, would be capable of achieving essentially the same result, although possibly after a somewhat longer time. Henceforth, a major influencing factor is a factor in which the binder loses its adhesive and/or cohesive capacity.

One type of binder in the form of a glue which will lose its adhesive and/or cohesive capacity during use is previously known from EP 0 571 548 B1. The temperature and pressure-sensitive glue in this document has what is known as a Normal Use Temperature Zone (NUTZ) which has a minimum temperature and a maximum temperature. The glue loses its adhesive and/or cohesive capacity completely or partly when the temperature either rises above the maximum temperature or falls below the minimum temperature, that is to say leaves the NUTZ range.

After the product has been fitted on the wearer, the body temperature of the wearer will raise the temperature in the absorbent product and in this way the temperature of the glue also. As a result, the temperature functions as a trigger or activating means for the glue and the leakage barriers. A suitable glue loses its adhesive and/or cohesive capacity within the range 27–40° C., preferably within the range 29–38° C. and most preferably within the range 30–37° C., wherein the first and/or second surface of the leakage barriers breaks away from its fastening surfaces and become a standing or raised leakage barrier. This minimizes the risk that (as in conventional diapers, incontinence products or other absorbent products with leakage barriers) the standing leakage barriers can end up askew when the absorbent product is put on the wearer, unnecessary leakage also being avoided in this way, or that the leakage barriers can end up partly over the liquid-permeable surface layer and thus prevent liquid from escaping down to the absorption body. Therefore, in a preferred embodiment of the present invention the risk of liquid running out of the product on or via the leakage barriers has also been reduced.

Other types of binders which could be used include waxes, oils or paraffins. Certain compositions which are today commonly included in, inter alia, lotions and skincare products can also be used (this does not exclude the possibility of considering using lotions and skincare products in their entirety, for example CAREMELT®, Henkel-Cognis, Sweden). Such compositions often have relatively low melting points which can easily be varied by changing the content in the composition. Suitable compositions can contain substances from groups consisting of glycerides, $C_{14}$–$C_{22}$ fatty alcohols, $C_{12}$–$C_{22}$ fatty acids and $C_{12}$–$C_{22}$ fatty alcohol ethoxylates with a degree of ethoxylation of roughly 2 to roughly 30, or derivatives thereof. In most cases, animal and vegetable oils contain a mixture of various saturated and unsaturated fatty acids. A person skilled in the art is very familiar with the possibility of influencing the melting point by increasing and/or decreasing the quantity of fatty acids in similar compositions, see table 1 and table 2 (values obtained from CRC Handbook of Chemistry and Physics $75^{th}$ edition 1994–1995 p. 7–28, 7–29).

TABLE 1

General content in various vegetable oils (% by weight).

| | | Saturated fatty acids (%) | | | | Unsaturated fatty acids (%) | | |
|---|---|---|---|---|---|---|---|---|
| Oil | Melting point (° C.) | $C_{12}$- Lauric acid | $C_{14}$- Myristic acid | $C_{16}$ - Palmitic acid | $C_{18}$- Stearic acid | $C_{16}$- Palmit-oleic acid | $C_{18}$- Oleic acid | $C_{18}$- Linoleic acid |
| Coconut oil | 25.1 | 45.4 | 18.0 | 10.5 | 2.3 | 0.4 | 7.5 | Trace |
| Cocoa butter | 34.1 | — | — | 24.4 | 35.4 | — | 38.1 | 2.1 |
| Palm oil | 35.0 | — | 1.4 | 40.1 | 5.5 | — | 42.7 | 10.3 |
| Palm kernel oil | 24.1 | 46.9 | 14.1 | 8.8 | 1.3 | — | 18.5 | 0.7 |

TABLE 2

Length of carbon chain and approximate melting point of various saturated and polyunsaturated fatty acids.

| Name | C atoms in chain | Melting point (° C.) |
|---|---|---|
| Saturated | | |
| Lauric acid | 12 | 43 |
| Myristic acid | 14 | 54 |
| Palmitic acid | 16 | 62 |
| Stearic acid | 18 | 69 |

TABLE 2-continued

Length of carbon chain and approximate melting point of various saturated and polyunsaturated fatty acids.

| Name | C atoms in chain | Melting point (° C.) |
|---|---|---|
| Unsaturated | | |
| Oleic acid | 18 | 13 |
| Linoleic acid | 18 | −9 |
| Palmitoleic acid | 16 | 0 |

A suitable composition for a preferred embodiment of the present invention loses its adhesive and/or cohesive capacity within the range 27–40° C., preferably within the range 29–38° C. and most preferably within the range 30–37° C.

It is also possible in a preferred embodiment of the present invention to use glue which loses its adhesive and/or cohesive capacity at TEWL values above 20 g/m²h. TEWL (transepidermal water loss) can be measured values above 20 g/m²h. TEWL (transepidermal water loss) can be measured using what is known as an evaporimeter (an EP2 from Servomed, Varberg, Sweden). The instrument is designed to measure the quantity of liquid which evaporates from the skin (in principle equivalent to the quantity transported through the skin) in g/m²h.

This value is commonly used as a measurement of the status of the skin with regard to the barrier function. However, the instrument can be used in association with products which cover the skin in order then to obtain a measurement of the moisture content on the surface of the skin (the measuring method is described in greater detail in "A refined method to evaluate diapers for effectiveness in reducing skin hydration—using the adult forearm", F. J. Akin et al., Skin research & technology, 1997; 3:173–176).

Instead of having a temperature-activated binder, the moisture content in the product can control the adhesive and/or cohesive properties of the binder. The moisture in an absorbent product can therefore be used in order to cause the glue to lose its adhesive and/or cohesive capacity. It is generally known that when the skin is covered by a material, the moisture content in the covered area increases. Alternatively, it is possible in a preferred embodiment of the present invention to use a glue which, when the moisture content becomes very high, that is to say equivalent to wetting of the product, loses its adhesive and/or cohesive capacity, that is to say the glue is water-soluble.

It is also possible in a preferred embodiment of the present invention to use glue which loses its adhesive and/or cohesive capacity at one or some values within the pH range 3–7. In addition to the fact that the skin has a specific pH, the pH of the urine, for example, can be used as the trigger for the glue to lose its adhesive and/or cohesive capacity.

According to another embodiment, the binder can be constituted by ultrasonic welding and/or a thermal bond of poor quality designed to lose its adhesive and/or cohesive capacity during use, for example when the product is subjected to mechanical action during use. It is also possible in a preferred embodiment of the present invention to conceive of the binder being constituted by ultrasonic welding and/or a thermal bond of good quality, executed in such a case with a smaller fastening surface than when the bond is made with poor quality. When the bond has been subjected to tensile and shear forces resulting from normal use of the absorbent product, it comes loose and loses its adhesive and/or cohesive capacity. A precondition for welding to be carried out is that materials to be welded have relatively alike melting points. Here, poor quality means, for example, a bond between two materials with relatively different melting points, that is to say, for example, that only one material melts and bonds to the other material, or that one material melts fully and the other only partly. Alternatively, it would be possible to consider that a bond of poor quality is formed when the energy supply is insufficient to melt the bonded material completely.

According to another embodiment, the binder consists of the binder of the leg elastic. When the leg elastic is fastened to the surface layers, this is usually performed using a hot-melt adhesive. If the quantity of this binder is not precisely adjusted, the binder can penetrate the surface layers in the leg portion, or escape at the edges of the leakage barriers. This excess quantity of binder can be used for fastening the leakage barriers.

According to one embodiment, the leakage barriers consist of or comprise a non-woven material or a laminate made of non-woven layers, which affords possibilities for great variation of the properties of the leakage barriers such as permeability, strength, softness and flexibility etc. A barrier laminate can of course also comprise materials other than non-woven layers, for example plastic film.

BRIEF DESCRIPTION OF THE DRAWINGS

Embodiments of the invention will be described in greater detail below with reference to the figures shown in the appended drawings, in which.

DETAILED DESCRIPTION OF THE PREFERRED EMBODIMENTS

The invention relates to all types of absorbent product intended to be placed in the crotch area of a wearer and to absorb bodily excretions. The invention therefore includes products such as diapers, pant diapers, incontinence pads or the like. It is principally a diaper which is described here.

Figure 1:
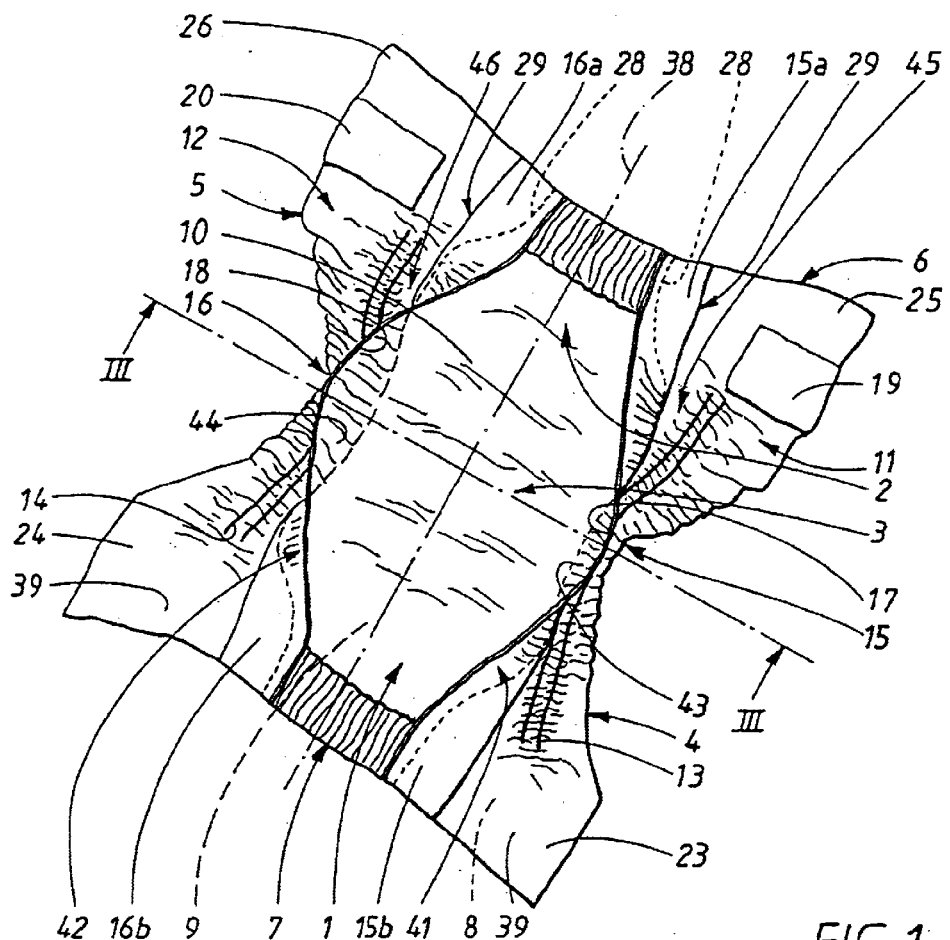
FIG. 1 shows a diaper before use, with the leakage barriers folded down and fastened to the side flaps and the second surface layer.

The diaper shown in FIG. 1 has a longitudinal center line and a transverse center line and has a front and a rear end portion 1, 2, an intermediate crotch portion 3, which is intended to be arranged between the legs of a wearer during use of the diaper, longitudinal side edges 4, 5 and transverse side edges 6, 7, a lower, liquid-impermeable backing layer 8, an absorption body 9, a first, liquid-permeable surface layer 10, and longitudinal leakage barriers 15, 16 fastened in the longitudinal direction along the liquid-permeable surface layer 10 on a first line 29 which constitutes or runs near to the first edge 45, 46 of the leakage barriers 15, 16. The leakage barriers 15, 16 also comprise a second edge 17, 18. The second edge 17, 18 contains elastic and is therefore gathered together at least in its central portion. Side flaps 11, 12 extend in the lateral direction outside the leakage barriers 15, 16 and, at least in the crotch portion 3, have longitudinal elastic elements 13, 14 along their free side edges 4, 5, which elastic elements 13, 14 serve as leg elastic during use of the product.

A first, essentially liquid-permeable surface layer 10 is positioned between the leakage barriers 15, 16, and a second, essentially liquid-impermeable surface layer 39 is positioned outside the leakage barriers 15, 16, the ends 15a, 15b, 16a, 16b of the leakage barriers being, in the example shown, folded down in the front end portion 1 and fastened flat against the first surface layer by a binder, for example glue or welding or the like, along a second line 28 which runs near to the second edge 17, 18 of the leakage barriers 15, 16 at least in part of the front end portion 1 and the rear end portion 2. Alternatively, it is possible to fasten down the ends 15a, 15b, 16a, 16b of the leakage barriers 15, 16 in only one of the end portions 1, 2. It is also possible to fasten the ends 15a, 15b, 16a, 16b to the liquid-impermeable surface layer 39.

The leakage barriers 15, 16 also have a first surface 41, 42 and a second surface 43, 44 between the ends 15a, 15b, 16a, 16b. The surface layers 10, 39 can be two different layers or alternatively the surface layers 10, 39 can be one and the same layer, but with greater liquid-permeability within an area which in FIG. 1 corresponds to the surface of the liquid-permeable surface layer 10. The diaper also comprises fastening arrangements 19, 20 (here folded in towards the surface layer of the diaper) in the form of tape with glue, or touch-and-close fasteners or the like. The diaper comprises side flaps 11, 12 which extend some way outside the leakage barriers.

The first edge 45, 46 of the leakage barriers 15, 16 is permanently fastened essentially along the liquid-permeable surface layer 10 on each side of the longitudinal center line 38 of the diaper but can also be fastened throughout the areas 15a, 15b, 15c, 16a, 16b. The fastening is effected by, for example, gluing or welding. In the embodiment in FIG. 1, the second edge 17, 18 of the leakage barriers is folded down outwards away from the longitudinal center line 38 of the product near to the crotch portion 3 of the diaper, and the first surface 41, 42 of the leakage barriers is fastened by a binder which loses its adhesive and/or cohesive capacity during use of the product.

Figure 2:
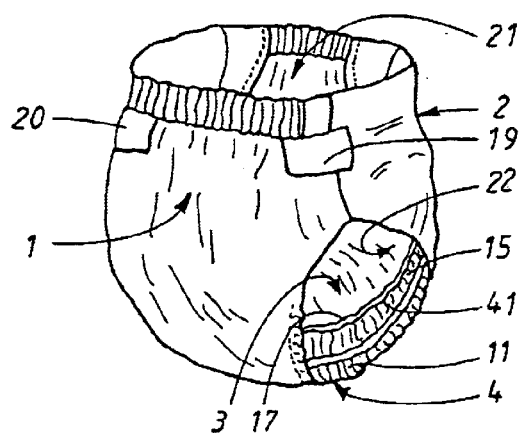
FIG. 2 shows a diaper as it appears during use, with the leakage barriers standing or raised.

FIG. 2 shows how the diaper will appear during use. Here, the front end portion 1 and the rear end portion 2 of the diaper can be seen, with the intermediate crotch portion 3. The front portion 1 is fastened together with the rear portion 2 by means of fastening arrangements 19, 20. This forms an opening 21 for the trunk of the wearer at the top of the diaper. An opening 22 for the leg of the wearer can also be observed in the figure. There is of course a corresponding leg opening 22 on that side of the diaper facing away from the observer in FIG. 2. At the edge of the opening 22 for the leg of the wearer, which is delimited by a side edge 4 on the product, a side flap 11 and a raised leakage barrier 15 can be seen, the first surface 41 of the leakage barrier 15 appearing clearly as the binder in its fastening surface has lost its adhesive and/or cohesive capacity, and the leakage barrier 15 has as a result assumed the form of a raised leakage barrier.

The leakage barrier 15, 16 is gathered, at least in its central part, by elastic elements which are fastened in a pretensioned state to the second edge 17, 18 of the leakage barrier 15, 16 and fastened at its ends 15a, 15b, 16a, 16b to the surface layer 10, 39. This means that when the product is extended around the wearer, and the glue which holds the second edge 17, 18 of the leakage barrier folded down comes away from its fastening surface, the leakage barrier will stand up and form a raised leakage barrier against the body of the wearer. The elastic is tensioned during use, which results in the second edge 17, 18 of the leakage barrier 15, 16 being directed upwards towards the wearer.

The leakage barriers 15, 16 are preferably essentially liquid-impermeable in order to prevent liquid from leaking out, principally in the crotch portion 3. As mentioned above, it can be a problem in the product on a wearer that the leakage barriers 15, 16 have a tendency to end up in the wrong place, that is to say to be folded in over the absorption body 9 and the surface layer 10 and thus to block these from the liquid and the excrement discharged by the wearer. This problem is eliminated as, according to the claimed invention, the second edge 17, 18 of the leakage barriers 15, 16 is folded down, and the first surface 41, 42 or second surface 43, 44 of the leakage barriers is fastened to the first surface layer 10 and/or the second surface layer 39 preferably near to the crotch portion 3 by a binder 50 which loses its adhesive and/or cohesive capacity during use of the absorbent product. The leakage barriers 15, 16 are then raised.

The areas located laterally outside the leakage barriers 15, 16 and the first line 29 are considered to be the side flaps 11, 12. In the front end portion 1 and rear end portion 2 of the diaper, the front ends 23, 24 and rear ends 25, 26 of the side flaps 11, 12 can be seen. The waist elastic shown in the figures can be present on one or both of the transverse edges 6, 7, but it is also possible for the diaper to have no waist elastic.

Figure 3A:
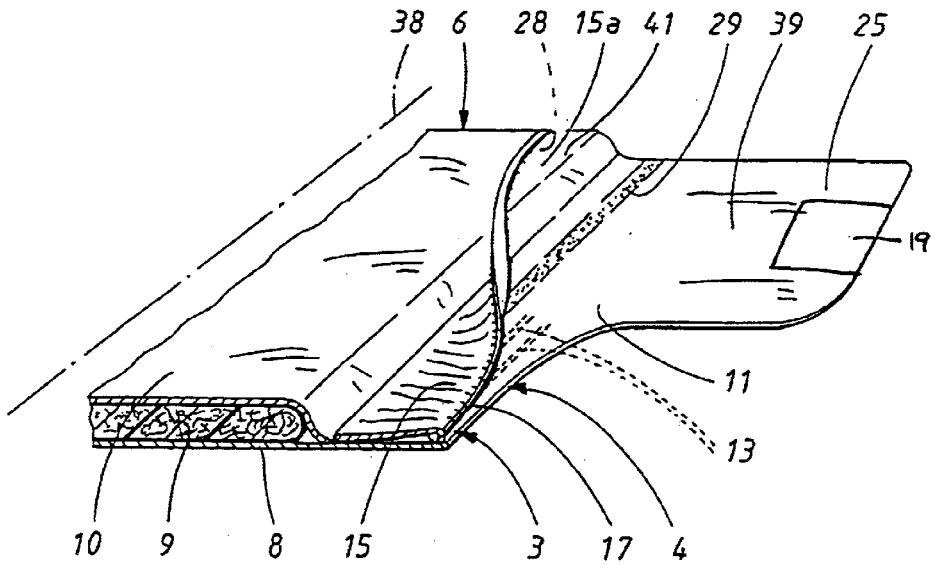
FIG. 3a shows a part of the front end portion of a diaper before use, comprising a leakage barrier which is folded down and fastened to the side flap and the second surface layer, in a side view.

FIG. 3a shows a part of a diaper before use, where the leakage barrier 15 shown and its stretchable second edge 17 are folded down near to the crotch portion 3 against the second surface layer 39, away from the longitudinal center line 38 of the product. The first surface 41 of the leakage barrier 15 is fastened by a binder, which loses its adhesive and/or cohesive capacity during use, to the side flap 11 and the second surface layer 39 near to the crotch portion 3.

In the cross-section of the diaper, the lower, liquid-impermeable backing layer 8, the absorption body 9 and the first, liquid-permeable surface layer 10 can be seen. A part of a longitudinal edge 4 and a transverse edge 6, a part of a side flap 11, with longitudinal elastic elements 13, the front end 25 of a side flap, and the end 15a of the leakage barrier, which end is folded down flat against the first surface layer 10, can also be seen. The second line 28 extends to a certain extent in the direction of the longitudinal center line 38 of the product, the end 15a of the folded-down leakage barrier being fastened to the first surface layer 10 along this second line. The fastening is suitably effected by gluing or welding, for example ultrasonic welding. It is also possible for the entire area 15a, between the first line 29 and the second line 28, to be fastened to the first surface layer 10 in the same manner, or only the first line 29 or alternatively the first line 29 and the second line 28 can be fastened in the same manner.

Figure 3B:
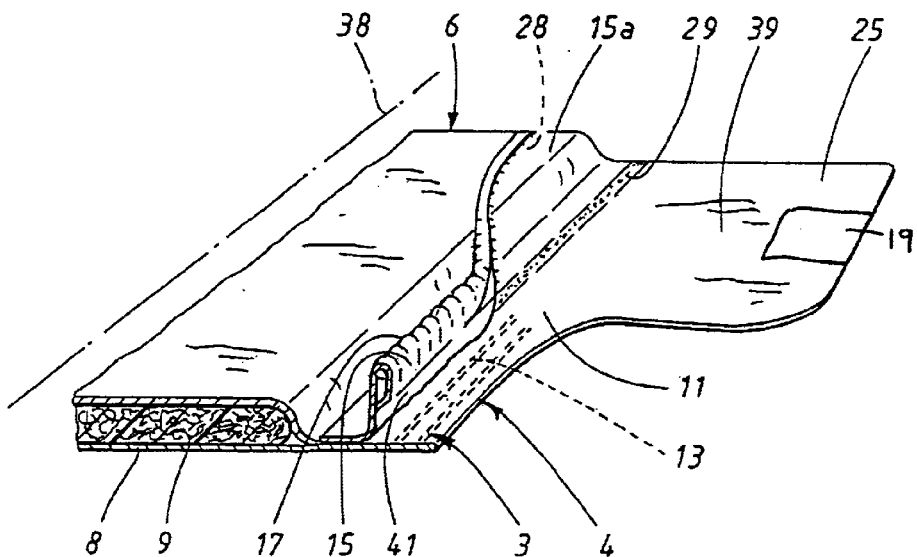
FIG. 3b shows a part of the front end portion of a diaper after use, comprising a leakage barrier which has come away from its fastening surface and become a standing or raised leakage barrier.

FIG. 3b shows a part of the diaper after use. The leakage barrier 15 and its stretchable second edge 17 are in the raised position, the first surface 41 of the leakage barrier 15 having come away from the side flap 11 and the second surface layer 39. In the cross-section of the diaper, the lower, liquid-impermeable backing layer 8, the absorption body 9 and the first, liquid-permeable surface layer 10 can be seen. A part of a longitudinal edge 4 and a transverse edge 6, with longitudinal elastic elements 13, the front end 25 of a side flap, and the end 15a of the leakage barrier, which end is folded down flat against the first surface layer 10, can also be seen. A second line 28 extends to a certain extent in the direction of the longitudinal center line 38 of the product, the end 15a of the folded-down leakage barrier being fastened to the first surface layer 10 along this second line. The fastening is suitably effected by gluing or welding, for example ultrasonic welding. It is also possible for the entire area 15a, between the first line 29 and the second line 28, to be fastened to the first surface layer 10 in the same manner. Alternatively, only the first line 29 or alternatively the first line 29 and the second line 28 can be fastened in the same manner.

Figure 4:
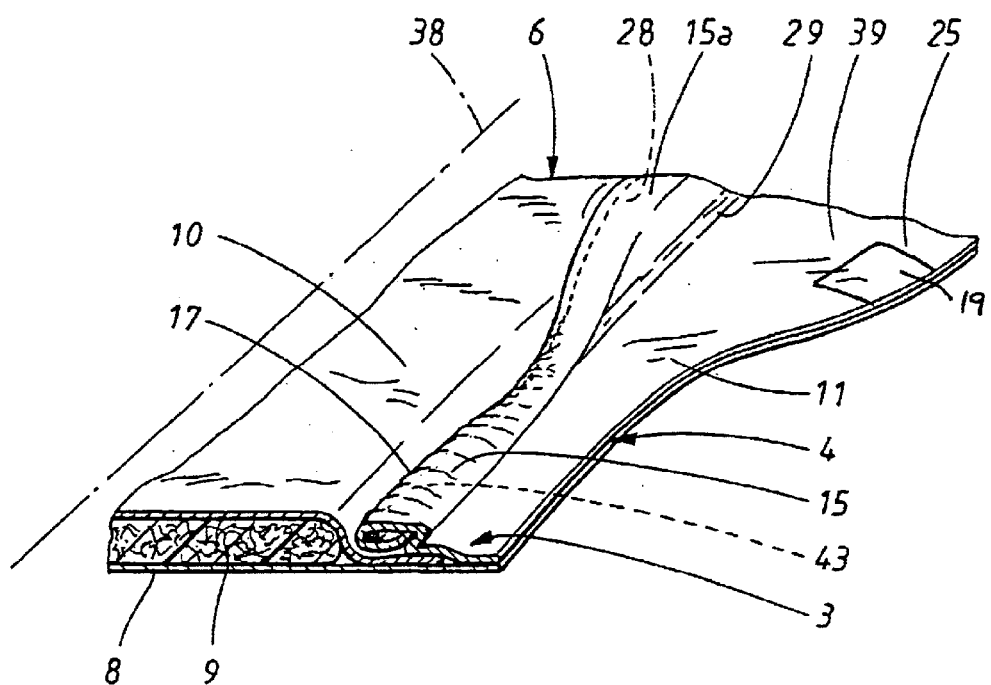
FIG. 4 shows a part of the front end portion of a diaper before use, comprising a leakage barrier which is folded down and fastened to the first surface layer.
Figure 5A:
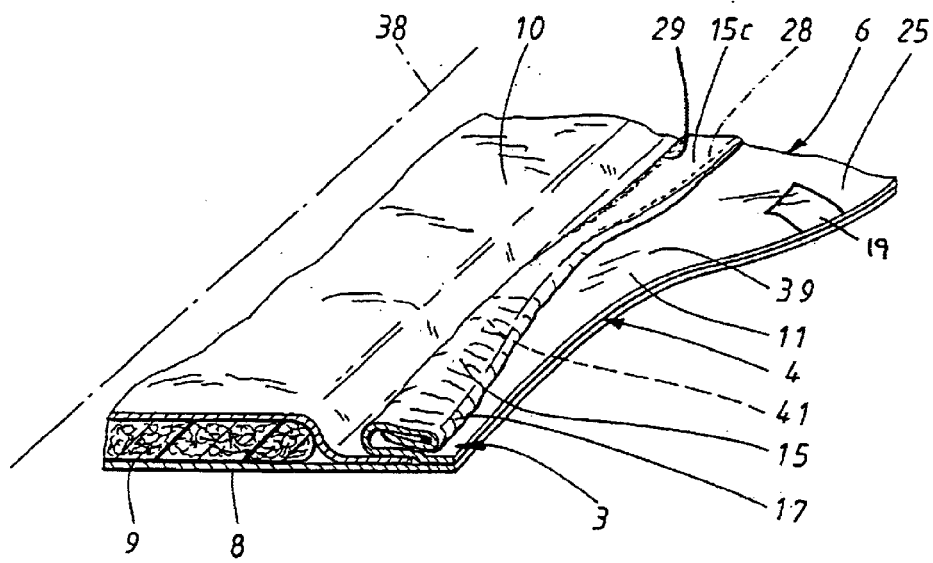
FIG. 5a shows a part of the front end portion of a diaper before use, comprising a leakage barrier which is folded down and fastened to the second surface layer.
Figure 5B:
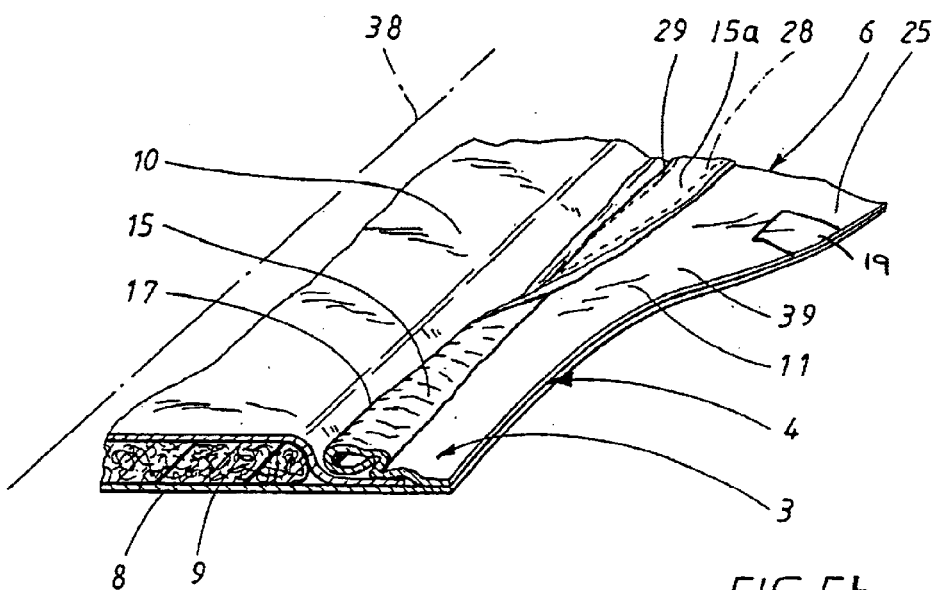
FIG. 5b shows a part of the front end portion of a diaper before use, comprising a leakage barrier which is folded down and fastened to the first surface layer.

It should be noted that FIGS. 4, 5a, and 5b show a different embodiment of the leakage barriers. This is in order to show that the invention is not limited to only one embodiment of leakage barriers but that all conceivable forms of leakage barrier can and are to be included within the scope of the invention. To the extent that a reference relates to a similar part, the same reference number is used as before.

FIG. 4 shows another embodiment of the invention before use, where the leakage barrier 15 and its stretchable second edge 17 are folded down near to the crotch portion 3, away from the second surface layer 39 and towards the longitudinal center line 38 of the product. The second surface 43 of the leakage barrier 15 is fastened by a binder, which loses its adhesive and/or cohesive capacity during use, to the first surface layer 10 near to the crotch portion 3. In the cross-section of the diaper, the lower, liquid-impermeable backing layer 8, the absorption body 9 and the second, liquid-impermeable surface layer 39 can be seen. A part of a longitudinal edge 4 and a transverse edge 6, a part of a side flap 11, the front end 25 of a side flap, and the end 15a of the leakage barrier, which end is folded down flat against the first surface layer 10, can also be seen. A second line 28 extends to a certain extent in the direction of the longitudinal center line 38 of the product, the end 15a of the folded-down leakage barrier being fastened to the first surface layer 10 along this second line. The fastening is suitably effected by gluing or welding, for example ultrasonic welding. It is also possible for the entire area 15a, between the first line 29 and the second line 28, to be fastened to the surface layer in the same manner, or the first line 29 or alternatively the first line 29 and the second line 28 can be fastened in the same manner.

FIG. 5a shows another embodiment of the invention before use, where the leakage barrier 15 and its stretchable second edge 17 are folded down against the second surface layer 39 near to the crotch portion 3, away from the longitudinal center line 38 of the product. The first surface 41 of the leakage barrier 15 is fastened by a binder, which loses its adhesive and/or cohesive capacity during use, away from the first surface layer 10, to the side flap 11 near to the crotch portion 3. In the cross-section of the diaper, the lower, liquid-impermeable backing layer 8, the absorption body 9, the first, liquid-permeable surface layer 10 and the second, liquid-impermeable surface layer 39 can be seen. A part of a longitudinal edge 4 and a transverse edge 6, the front end 25 of a side flap, and the end 15a of the leakage barrier, which end is folded down flat away from the first surface layer 10, can also be seen. A second line 28 extends to a certain extent in the direction of the longitudinal center line 38 of the product, the end 15a of the folded-down leakage barrier being fastened to the second surface layer 39 along this second line. The fastening is suitably effected by gluing or welding, for example ultrasonic welding. It is also possible for the entire area 15a, between the first line 29 and the second line 28, to be fastened to the second surface layer 39 in the same manner, or only the first line 29 or alternatively the first line 29 and the second line 28 can be fastened in the same manner.

FIG. 5b shows another embodiment of the invention before use, where the leakage barrier 15 and its stretchable second edge 17 are folded down against the first surface layer 10 near to the crotch portion 3, away from the longitudinal center line 38 of the product. The second surface 43 (not shown) of the leakage barrier 15 is fastened by a binder, which loses its adhesive and/or cohesive capacity during use, to the first surface layer 10, away from the side flap 11 near to the crotch portion 3.

In the cross-section of the diaper, the lower, liquid-impermeable backing layer 8, the absorption body 9, the first, liquid-permeable surface layer 10 and the second, liquid-impermeable surface layer 39 can be seen. A part of a longitudinal edge 4 and a transverse edge 6, the front end 25 of a side flap, and the end 15c of the leakage barrier, which end is folded down flat away from the first surface layer 10, can also be seen. A second line 28 extends to a certain extent in the direction of the longitudinal center line 38 of the product, the end 15c of the folded-down leakage barrier being fastened to the second surface layer 39 along this second line. The fastening is suitably effected by gluing or welding, for example ultrasonic welding. It is also possible for the entire area 15c, between the first line 29 and the second line 28, to be fastened to the surface layer in the same manner. In a corresponding manner, only the first line 29 or alternatively the first line 29 and the second line 28 can be fastened in the same manner.

A fiber fabric material, i.e., a non-woven material, is usually used as a surface layer in absorbent products, such as diapers and incontinence pads. It is also possible, however, to use perforated plastic film, net material, open-cell foam or the like. It is also possible to use absorption materials with a surface which also functions as a liquid-permeable surface layer. Examples of such absorption materials are absorbent open-cell foam, bound fiber wadding or the like. A fiber fabric material which is often used as a surface material on absorbent products is fiber fabric made of polypropylene fibers. This material is hydrophobic, which means that, in the untreated state, it tends not to admit liquid. It is a suitable material for, for example, the leakage barriers 15, 16 and the surface layer 39 of the side flaps 11, 12, which are preferably liquid-impermeable. The surface layer in a diaper can consist of the same material over the entire surface, both inside and outside the leakage barriers, as well as in the leakage barriers, which are then folded from the surface material with an elastic thread included as an elastic element which produces the gathered part of the leakage barriers.

Liquid will be admitted on the surface layer between the two leakage barriers 15, 16. The side flaps 11, 12, including their front and rear ends 23, 24, 25, 26, are located outside the leakage barriers 15, 16. As mentioned above, a fiber fabric made of polypropylene is hydrophobic and thus essentially liquid-impermeable, which is suitable for the side flaps and the leakage barriers as these are preferably to be liquid-impermeable. In the liquid-receiving area between the two leakage barriers 15, 16, it must be possible for liquid to penetrate in order to reach the absorption body 9. Here, the surface layer has been treated so that it is hydrophilic and thus tends to admit liquid and allow it through to the underlying absorption body 9. A fiber fabric made of polypropylene can be treated in a conventional manner so that it becomes hydrophilic.

The first and second surface layers 10, 39 can consist of one and the same layer which extends over the entire diaper. Then, either the part which constitutes the first surface layer 10 between the leakage barriers 15, 16 is treated so that it becomes liquid-permeable, or the part which constitutes the second surface layer 39 is treated so that it becomes essentially liquid-impermeable. The leakage barriers 15, 16 can also consist of this layer, consisting of the same material type or different material types. If the same material type is used, the different layers 10, 39 can have, for example, a different fiber content so that the materials differ in terms of impermeability or thickness and allow liquid through to a greater or lesser extent. In this connection, a more impermeable material is then selected in the areas which are to be liquid-impermeable, that is to say the surface layer 39 of the side flaps 11, 12 and their front and rear ends 23, 24, 25, 26 and, if appropriate, the leakage barriers 15, 16. A less impermeable material is used on the liquid-receiving surface layer 10 which is located between the two leakage barriers 15, 16. The materials can be hydrophobic or hydrophilic from the outset, and the hydrophobic material is selected where the material is to be liquid-impermeable, and the hydrophilic material is selected where the material is to be liquid-permeable. The leakage barriers 15, 16 can also consist of a number of different layers. If the first layer is a fiber fabric made of, for example, spunbond non-woven, which is common today, a material layer can be applied by means of a meltblown technique, which layer is liquid-impermeable, and then another layer of fiber fabric can be applied. In a meltblown technique, a molten polymer is extruded in a hot gas stream at high speed, which transforms the polymer into fibers which are cooled and collected to form a fabric or web which is in this case then bound together with a web of fiber fabric. An example of such materials is what is known as SMS (spunbond-meltblown-spunbond) material. This type of layer material can also be used as the surface layer 39 on the side flaps 11, 12 which are also essentially liquid-impermeable. Other types of liquid-impermeable material can of course also be used in these areas, in the same way as it is possible to use different liquid-permeable materials in the surface layer 10 between the leakage barriers 15, 16.

In the embodiment shown, the absorption body 9 consists of cellulose fluff with or without what are known as superabsorbent products mixed in. However, the absorption body can be made of any material(s) used in absorption bodies for absorbent products such as diapers, pant diapers, incontinence pads, panty liners or the like. The absorption body 9 can also consist of more than one layer of absorbent material and can also contain layers of wadding material or the like so as to be capable of conducting discharged liquid away from the liquid-receiving surface layer 10 rapidly. Each of the layers of the absorption body 9 can of course contain superabsorbents.

The liquid-impermeable backing layer 8 can consist of or comprise a liquid-impermeable plastic film, a non-woven layer coated with a liquid-blocking material, or some other flexible material layer which has the capacity to resist liquid penetration. It is in general an advantage if the liquid-impermeable backing layer 8 is breathable, that is to say allows water vapour to pass through the layer 8.

The invention therefore relates to an absorbent product with improved characteristics with regard to the positioning of the leakage barriers 15, 16 and the design for putting the product on the wearer. The leakage barriers 15, 16 and their stretchable second edge 17, 18 are folded down away from and/or towards the longitudinal side edge 4, 5 of the product towards and/or away from the longitudinal center line 38 of the product. The first surface 41, 42 and/or second surface 43, 44 of the leakage barriers 15, 16 are fastened near to the side flaps 11, 12 and the first surface layer 10 and/or second surface layer 39 near to the crotch portion 3 by a binder 50 which loses its adhesive and/or cohesive capacity during use of the product. The folding down of the leakage barriers 15, 16 reduces the risk of the leakage barriers positioning themselves over the liquid-permeable surface layer 10 and thus minimizing bodily fluids and excrement from the wearer from reaching the absorption body 9. The risk of leakage of bodily fluids, excrement, unpleasant sensations and skin irritations on account of close contact with excrement, etc. is therefore reduced.

Although this invention has been illustrated and described in accordance with certain preferred embodiments, it is recognized that the scope of this invention is to be determined by the following claims and equivalents thereof.

What is claimed is:

1. An absorbent product comprises an absorption body having a generally oblong shape with two longitudinal sides, two transverse sides, a longitudinal center line,
    a first liquid-permeable surface layer,
    a second essentially liquid-impermeable surface layer,
    an essentially liquid-impermeable backing layer,
    an absorption body positioned between said liquid-permeable surface layer and said backing layer, and
    two leakage barriers made of flexible material and extending in the longitudinal direction with one of the barriers on each side of the longitudinal center line and the liquid-permeable surface layer,
    each of the leakage barriers having a first edge permanently fastened along the liquid-permeable surface layer and a second edge which extends in the direction of the longitudinal center line of the absorbent product, the second edge contains elastic so as to gather the second edge at least in a central portion thereof,
    each of the leakage barriers also having a first surface and a second surface, wherein one of the first surface and the second surface of each of said leakage barriers is fastened to or near to one of the first, liquid-permeable surface layer and the second, liquid-impermeable surface layer in a temporary manner by a binder having an adhesive or cohesive capacity which is lost during use of the absorbent product, wherein the one of the first surface and the second surface of each leakage barrier comes away from the one of the first surface layer and the second surface layer it is fastened to and forms a raised leakage barrier due to the gathering by said elastic when adhesive or cohesive capacity of the binder is lost, wherein the adhesive or cohesive capacity of the binder is lost within the temperature range 30–37° C.

2. The absorbent product according to claim 1, wherein the binder is oil, wax or glue.

3. The absorbent product according to claim 2, wherein the binder is a glue.

4. The absorbent product according to claim 1, wherein the binder comprises glycerides or $C_{14}$–$C_{22}$ fatty alcohols.

5. The absorbent product according to claim 1, whereas the binder is a mixture of saturated and unsaturated $C_{12}$–$C_{22}$ fatty acids.

6. The absorbent product according to claim 1, wherein the leakage barriers comprise a non-woven material or laminate thereof.

7. The absorbent product according to claim 1, wherein the binder comprises $C_{12}$–$C_{22}$ fatty acids.

8. The absorbent product according to claim 1, wherein the binder comprises $C_{12}$–$C_{22}$ fatty alcohol ethoxylates with a degree of ethoxylation of roughly 2 to roughly 30.

9. The absorbent product of claim 1, wherein the absorbent product is a diaper, a pant diaper, an incontinence pad or, a sanitary towel.

10. The absorbent product according to claim 1, wherein the binder comprises derivatives of glycerides or $C_{14}$–$C_{22}$ fatty alcohols.

11. The absorbent product according to claim 1, wherein the binder comprises derivatives of $C_{12}$–$C_{22}$ fatty acids.

12. The absorbent product according to claim 1, wherein the binder comprises derivatives of $C_{12}$–$C_{22}$ fatty alcohol ethoxylates with a degree of ethoxylation of roughly 2 to roughly 30.

13. The absorbent product according to claim 1, wherein the binder loses its adhesive or cohesive capacity at TEWL values above 20 g/m²h.

14. An absorbent product comprises an absorption body having a generally oblong shape with two longitudinal sides, two transverse sides, a longitudinal center line, a first liquid-permeable surface layer, a second essentially liquid-impermeable surface layer, an essentially liquid-impermeable backing layer, an absorption body positioned between said liquid-permeable surface layer and said backing layer, and two leakage barriers made of flexible material and extending in the longitudinal direction with one of the barriers on each side of the longitudinal center line and the liquid-permeable surface layer, and each of the leakage barriers having a first edge permanently fastened along the liquid-permeable surface layer and a second edge which extends in the direction of the longitudinal center line of the absorbent product, each of the leakage barriers also having a first surface and a second surface, wherein one of the first surface and the second surface of each of said leakage barriers is fastened with a binder to or near to one of the first, liquid-permeable surface layer and the second, liquid-impermeable surface layer, wherein the adhesive or cohesive capacity of an binder is lost at TEWL values above 20 g/m²h.

15. The absorbent product according to claim 14, wherein the binder is oil, wax or glue.

16. The absorbent product according to claim 15, wherein the binder is a glue.

17. The absorbent product according to claim 14, wherein the binder comprises glycerides or $C_{14}$–$C_{22}$ fatty alcohols.

18. The absorbent product according to claim 14, whereas the binder is a mixture of saturated and unsaturated $C_{12}$–$C_{22}$ fatty acids.

19. The absorbent product according to claim 14, wherein the leakage barriers comprise a non-woven material or laminate thereof.

20. The absorbent product according to claim 14, wherein the binder comprises $C_{12}$–$C_{22}$ fatty acids.

21. The absorbent product according to claim 14, wherein the binder comprises $C_{12}$–$C_{22}$ fatty alcohol ethoxylates with a degree of ethoxylation of roughly 2 to roughly 30.

22. The absorbent product of claim 14, wherein the absorbent product is a diaper, a pant diaper, an incontinence pad, or a sanitary towel.

23. The absorbent product according to claim 14, wherein the binder comprises derivatives of glycerides or $C_{14}$–$C_{22}$ fatty alcohols.

24. The absorbent product according to claim 14, wherein the binder comprises derivatives of $C_{12}$–$C_{22}$ fatty acids.

25. The absorbent product according to claim 14, wherein the binder comprises derivatives of $C_{12}$–$C_{22}$ fatty alcohol ethoxylates with a degree of ethoxylation of roughly 2 to roughly 30.

26. The absorbent product according to claim 14, wherein the binder loses its adhesive or cohesive capacity within the temperature range 30–37° C.

* * * * *